(12) United States Patent
Sudge

(10) Patent No.: US 6,408,850 B1
(45) Date of Patent: Jun. 25, 2002

(54) MEDICAL TUBE HOLDER APPARATUS

(76) Inventor: Michael Sudge, 653 #C Idlewild Cir., Birmingham, AL (US) 35205

( * ) Notice: Subject to any disclaimer, the term of this patent is extended or adjusted under 35 U.S.C. 154(b) by 0 days.

(21) Appl. No.: 08/184,212

(22) Filed: Jan. 21, 1994

Related U.S. Application Data

(63) Continuation-in-part of application No. 08/015,555, filed on Feb. 9, 1993, now abandoned.

(51) Int. Cl.⁷ .............................................. A61M 16/00
(52) U.S. Cl. .............................. 128/207.17; 128/207.14
(58) Field of Search ....................... 128/207.14–207.18, 128/DIG. 26, 911, 912

(56) References Cited

U.S. PATENT DOCUMENTS 4,270,529 A * 6/1981 Muto .................... 128/200.26
4,774,944 A * 10/1988 Mischinski ................. 128/912

OTHER PUBLICATIONS

OHIO Chemical Catalog, 1964, Form No. 9710, Stock No. 178–5705–000, 1400 E. Washington Ave., Madison, WI, 53701, p. 40.*
Webster's Ninth New Collegiate Dictionary, 1986, Merriam–Webster Inc., Springfield, MA, p. 199.*

* cited by examiner

Primary Examiner—John G. Weiss
Assistant Examiner—Teena Mitchell
(74) Attorney, Agent, or Firm—Thad G. Long; Greg Peterson

(57) ABSTRACT

A one-piece medical tube holder apparatus which fastens securely about a medical tube through straightforward interlocking joining of male/female ends, with means for attaching a harness assembly, and an optional notch for securing an auxiliary medical tube, the holder being releasable by deliberate action laterally of the male/female ends.

21 Claims, 4 Drawing Sheets

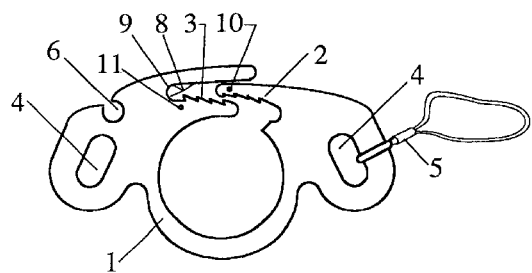
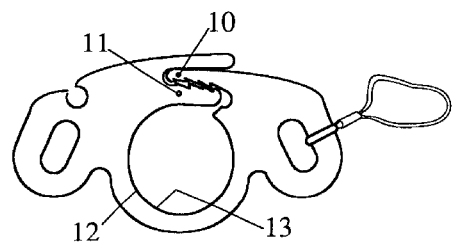
Figure 1
Figure 2
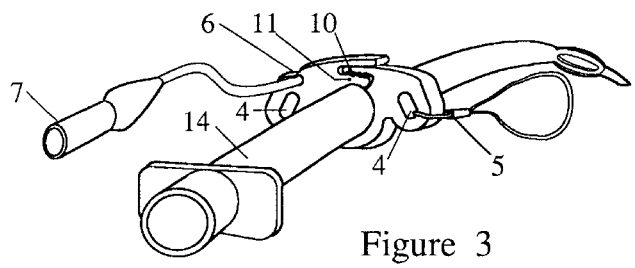
Figure 3
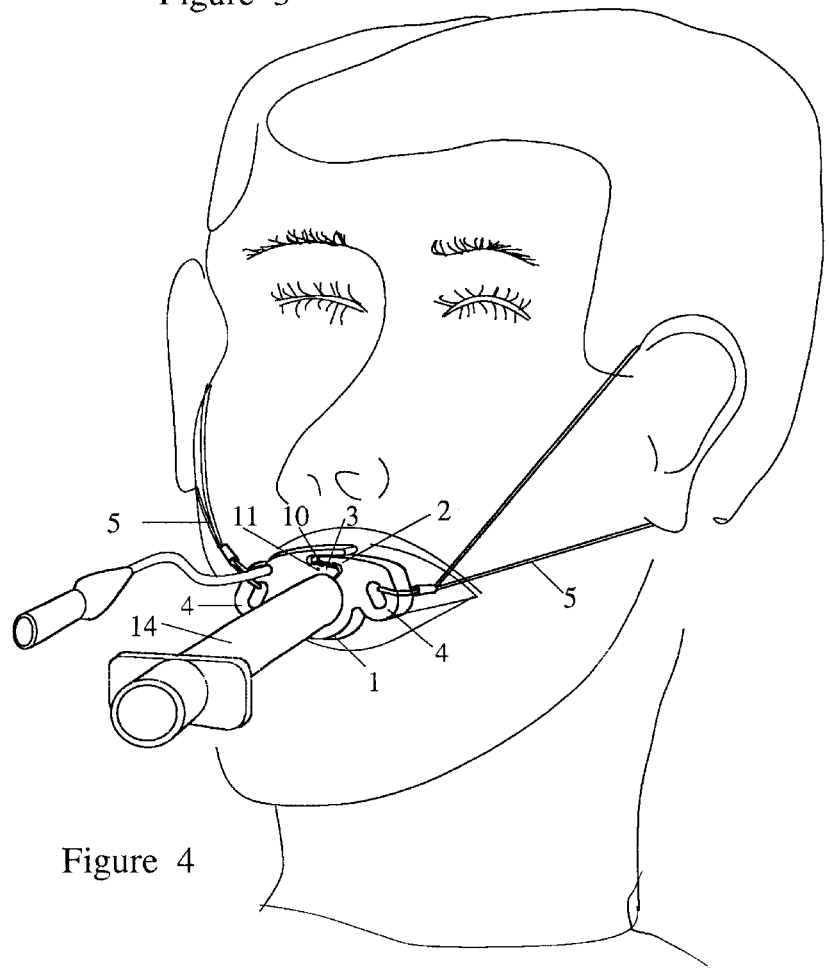
Figure 4

MEDICAL TUBE HOLDER APPARATUS

This application is a continuation-in-part of U.S. Ser. No. 08/015,555, filed Feb. 9, 1993 and entitled "Medical Tube Holder Apparatus," which is copending and is hereby abandoned.

BACKGROUND

This invention relates to the field of fixating fitments or holder apparatus for medical tubes, such as medical breathing tubes. It is often a medical necessity to establish an artificial airway in a person with breathing difficulties. Such artificial airway is commonly accomplished by the insertion, via the mouth or nose, of a breathing tube into the trachea. Such breathing tube is often referred to as an endotracheal or tracheal tube. After insertion, it then becomes necessary to secure, fixate and stabilize the tube so that the tube does not migrate out of nor too deeply into the trachea, or cause other complications.

The most common method of fixating a breathing tube is to use adhesive tape. The disadvantages to using adhesive tape are manifold, not the least of which is difficulty in learning effective techniques for applying the tape properly. Length of time in applying, the need for preparing the patient's skin with chemicals so the tape will adhere, and the need for removing facial and other body hair are techniques which must be learned and which take time to carry out in actual practice, where time can be a vital consideration. There is also associated breakdown of the taping system and the erosion and/or necrosis of skin, lips and other tissues.

If the tracheal tube must be repositioned or changed, which frequently must be done, all old tape and its residues must be removed and steps for re-taping taken. The adhesive tape must be frequently changed for positioning or for hygienic or appearance reasons. The use of adhesive tape can also be very time consuming for the doctors, patient care technicians and nurses, as in most cases it takes several minutes to fixate the tube and it often requires two persons to apply: one to hold the tube in position, while the other fixates the tube.

Some other disadvantages of adhesive tape are that it is affected by body secretions and other liquids, body temperatures, changes in patient's anatomy from swelling or surgical procedures, and the position of the patient.

Any one or a combination of the aforementioned disadvantages can cause great discomfort to the patient and can directly or indirectly result in inadvertent or undesirable displacement of the tracheal tube. This displacement can cause loss or reduced effectiveness of the artificial airway, thus frequently leading to emergency medical situations and even to loss of life.

In current medical practice, more patients are being tracheally and/or endotracheally intubated and for longer periods of time than formerly. These longer time periods have greatly increased the importance of maintaining tube position, performing oral care, and maintaining and preserving the integrity of all tissues and surfaces that are involved.

There have been many attempts to overcome the problems associated with fixating and maintaining tracheal tubes through the use of fixating, holding and securing devices.

Some of these previous attempts include, but are not limited to: U.S. Pat. No. 3,602,227 (Andrew); U.S. Pat. No. 3,760,811 (Andrew); U.S. Pat. No. 3,993,081 (Cussell); U.S. Pat. No. 4,249,529 (Nestor); U.S. Pat. No. 4,284,076 (Hall); U.S. Pat. No. 4,351,331 (Gereg); U.S. Pat. No. 4,392,858 (George); U.S. Pat. No. 4,449,527 (Hinton); U.S. Pat. No. 4,483,337 (Clair); U.S. Pat. No. 4,683,882 (Laird); U.S. Pat. No. 4,744,358 (McGinnis); U.S. Pat. No. 5,076,269 (Austin); U.S. Pat. No. 5,069,206 (Crosbie); and U.S. Pat. No. 5,026,352 (Anderson). Two other patents were considered relevant by the Examiners in the above-reference U.S. Ser. No. 08/015,555, of which this is a continuation-in-part: U.S. Pat. Nos. 2,908,269 (Cheng); and 4,872,579 (Palmer). Certain other patents were cited by said Examiners as being "of interest".

Many of the devices proposed in these patents are uncomfortable to the patient, do not reliably maintain the tube in proper position at all times, restrict patient movement, and are difficult to apply and reapply or reposition. Many of the devices also include inherent design flaws that can easily compromise the basic safety of the patient, and make maintenance of all associated tissues and surfaces difficult.

Some devices, such as the Crosbie, Gereg and McGinnis patents, disclose a device which includes a "bite block". However, only a very small percentage of patients require a bite block For the greatest number of patients, it is yet another intrusion into the oral area which creates more difficulties and discomfort.

The Crosbie patent also discloses a device that may quite readily cause pinching of the tracheal tube, thus narrowing the internal lumen of the tube and occluding or restricting the flow of gas to the point that it easily may be detrimental to a patient's ability to exchange gas, thus itself seriously compromising respiration. Crosbie relies on a component living hinge to allow the opening and closure of two rigid half disks with discrete cutaway spaces for engaging tubes of a size to engage snugly within the predetermined spaces on closure of the half disks. This device is extremely cumbersome and has little practical utility.

The Austin patent discloses a two-piece tracheal tube retaining device which requires a ring clamp type mechanism and a special separate collar in order to be operative. It is awkward to apply, can be uncomfortable to the patient because of the torque exerted by the harness at the "ears" of the collar where the harness is attached, and can irritate the patient's mouth because it is designed to engage the patient's lips. It also obstructs medical observation of the lip.

The Hinton patent discloses a tracheal tube holder which has an interior which is of a spongy material which should be avoided for hygiene reasons. The clamp device of the patent would significantly obstruct the patient's mouth at the lower part of the tube.

The McGinnis tube holder patent discloses a bulky system that is obstructive to the mouth and requires a large and complex head gear system to hold the tube in place.

The Anderson patent discloses a tube fitment device which has a flange plate which is obstructive to oral areas.

The Cheng patent appears to lack any discernible relevance. It has a passageway through which a tube can be guided to an interior portion of a metal plate and then locked in place with a shoe and cam. But it is not suitable for, nor suggestive of, a device which provides for the securing of an auxiliary tube at or near the upper edge of the plate.

Palmer does not relate at all to endotracheal tube holders but rather to a ventilating and aspirating assembly. It has markers which merely indicate "open" and "closed" alignment of two concentric cylinders, and does not in any way disclose or suggest markers in the present invention which indicate degrees of tightness of a ring of shrinking circumference.

SUMMARY

It is the general object of the present invention to provide a medical tube holder apparatus which fixates a medical tube and alleviates the problems mentioned above.

A tube fixating device in accordance with the present invention is quickly and easily applied, and is economical to manufacture and use.

The device is reliable for holding the tube in position while maximizing patient comfort and for maintaining the integrity of the associated tissues.

According to one embodiment of the present invention, there is provided a medical tube fixator/fitment device or medical tube holder apparatus of a flexible, resilient material with no component hinge in a generally circular flexible elongated strip shape with releasable locking members (but, for patient security, not transversely releasable) and ported securing ears located on each end so that the ends of the circle may be joined, causing the interior wall of the device to grip or grasp the tube. Included on the interior wall of the circular device are ridges or other good frictional surface to grip better the exterior wall of a tube. Another aspect of the present invention is a travel limiting locking device which prevents occlusion of a medical tube. A circular shaped device is considered the preferred embodiment because the tubes to be engaged are generally circular or cylindrical, and a circular fixating device can engage and touch more points on the circumference of the tube i.e., substantially the entire circumference of the tube at the location of the engagement, than can other configurations and thus provide more friction.

Another aspect of the present invention is a positioner notch which is located on one of the ends of the circular device for the placement and retention of a cuff inflation line or other auxiliary medical tube which is often used in conjunction with an endotracheal tube.

Yet another aspect includes alignment dots, dimples or other markings to indicate that the tube fixating device or holder apparatus is in an appropriately closed or locked position appropriate to the size of the tube for which it is designed to be used. This prevents undue looseness, on the one hand, and undue tightness which might pinch and narrow the interior passage area of the tube.

The fixating devices or holder apparatus may also be color coded or otherwise coded for size so that the possibility of error in matching the devices to the appropriately sized tubes is minimized.

An object of the present invention is to provide a device or apparatus which is not affected by facial hair, body secretions or other liquids, facial anatomy, or body temperatures and maintains the medical tube in a reliably stable and secure position. The need to shave the skin or prepare it with chemicals is eliminated.

A further object of the present invention is to provide a device or apparatus which may be randomly positioned so as to allow for an endotracheal tube to be positioned toward or away from a specific part of the anatomy—for example, keeping the tube positioned to one side of the face when surgery is being or has been performed on the other, or retaining the tube in nasal insertion mode as opposed to oral insertion mode.

In accordance with the invention, the tube fixating device or medical tube holder apparatus is of relatively small size and low profile, weighing less than one ounce and having a cross-sectional thickness of the strip portion of the invention less than one centimeter, so that obstruction of the oral or facial area is minimized and medical observation of the patient's mouth area is facilitated. The device is also inexpensive.

The retention system of the present invention provides a versatile means of securing the device to the patient's head and neck. A suggested harness assembly is provided in the following illustrations, but other means such as string or small diameter flexible tubing may be employed.

Other objects and advantages appear in the following description and may be readily appreciated when considered in connection with the accompanying drawings.

BRIEF DESCRIPTION OF THE DRAWINGS

FIG. 1 is a side view of a preferred embodiment of the invention in an open position.

FIG. 2 is a side view of a preferred embodiment of the invention in a fully closed position.

FIG. 3 shows a preferred embodiment of the invention engaging an artificial airway tube.

FIG. 4 shows a preferred embodiment of the invention engaging an artificial airway tube, prepared for holding the tube in place for a medical patient.

DETAILED DESCRIPTION OF THE DRAWINGS

Figure 5:
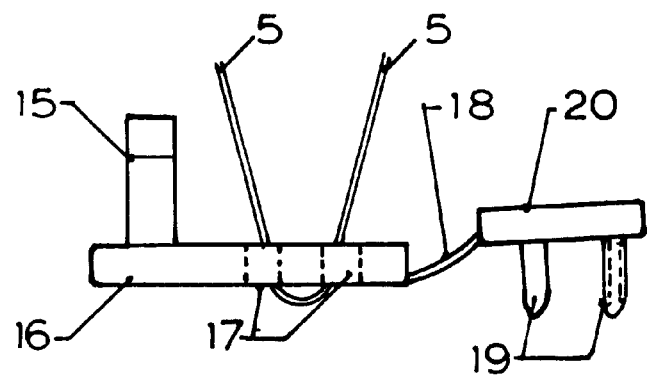
FIG. 5 shows a narrow side view of a device for affixing a harness to a medical tube holder apparatus, in an open position.

In FIG. 1, the medical tube holder apparatus comprises a generally circular device 1 of a flexible, resilient material that has a region that is adapted to embrace a portion of a tube, with a releasable male locking component 2 and female locking component 3. Near each locking component is an ear 4 with an opening for receiving a securing device 5, such as a harness whose ends are attached to the respective openings in ears 4. An optional notch 6 is for convenient placement of a tracheal tube cuff inflation line 7 or other auxiliary medical tube which may be used in conjunction with the primary medical tube.

The releasable female locking component 3 comprises grooves 8 located on one end of the device 1 which receives a serrated male locking component 2 from the other end of said device. The component 2 can travel no further than the depth of the receiving end stop 9 of component 3, which limits the interior diameter of the semi-circle so that occlusion of the medical tube does not occur. While the locking components are releasable by moving the female and male locking components 3 and 2 in opposite directions generally parallel with the axis of the medical tube, they are not releasable by motion which merely reverses the path by which they are locked, i.e., motion transverse to the axis of the medical tube.

FIG. 2 shows a preferred embodiment of the invention in a closed position. FIG. 2 also shows, as an optional feature, located on the pistil tip of the male locking component 2, an indicator dot or dimple 10. A second indicator dot or dimple 11 may be located on the receiving groove of female locking component 3. The alignment of these dots serves as a safety check feature to indicate that the fixator is in the fully closed or locked position and is neither too tight nor too loose about an appropriately sized medical tube. While the flexible and resilient circular strip of the present invention inherently makes the invention suitable for satisfactory engagement of tubes having a range of diameters, it will often be desirable to mark positions for engagement of certain tubes of frequently used diameters so as to add speed and certainty to engagement with such popular sizes.

The interior wall 12 of the device is designed to grasp the exterior wall of a tracheal tube by means of ridges or grooves or other friction means 13 to enhance the grasp of the medical tube so that the fixator or holder apparatus does not slide up, down or around the tube.

FIG. 3 shows a preferred embodiment of the invention as described in FIGS. 1 and 2 above, engaging the exterior wall of a medical tube 14 in a locked position with a harness or other securing device 5 attached to the invention through openings in ears 4 and also a tracheal tube cuff inflation line 7 attached to the invention in notch 6.

FIG. 4 shows the invention, as depicted in FIG. 3, in use as a tracheal tube holder apparatus with respect to a medical patient in whom the tracheal tube is functioning as an artificial airway.

In use, the patient end of an appropriately sized tracheal tube 14 is inserted into a patient's trachea in the usual way i.e., through mouth or nasal passage. The medical tube holder apparatus 1, while in the open or unlocked position, may then be slid down the machine end of the tube 14, or the ears 4 of each end of the apparatus may be grasped, outward pressure then exerted, further opening the male and female locking components 2 and 3, and the apparatus 1 then slid around the exterior wall of the tube 14.

The apparatus 1 is then slid toward the patient to a point that it is near but not touching the patient. The operator then selects a position for the ears 4 by rotating the apparatus. After a position for the apparatus 1 is chosen, the ears 4 are grasped between thumb and finger, pressure is exerted inwardly causing the component 2 and component 3 to lock. The apparatus resists opening, and generally will not open, when tension is exerted along the same line or path through which pressure was exerted in the locking operation. The device is thus secured about tube 14.

For the appropriate size apparatus 1 for a tracheal tube 14, the dots or dimples or other markings 10 and 11 are pre-positioned so that they will align when fastened properly by interlocking male and female components 2 and 3, and the apparatus 1 will firmly grasp the tube 14 connected through the ear 4 openings of harness strap 5 which fits about the patient's head and neck. The alignment is a safety check to help insure that the apparatus is neither too loose nor too tight about the medical tube. String, elastic material, fabric tape, plastic type tubing, or numerous other well known devices can function as a harness strap. An example of a harness facilitating device will be discussed below in connection with FIGS. 5, 6, 7, 8, 9 and 10.

For removal of the tube, or to release the grasp of the medical tube holder apparatus, one merely applies opposing side-to-side pressure on components 2 and 3 generally along lines parallel with the axis of tube 14. The interlocking components 2 and 3 will disengage laterally as a result of this deliberate action, while remaining securely locked against pressures and tensions exerted in a direction transverse to the axis of tube 14, along which direction it became locked. The apparatus may thus be removed, or the tube may be repositioned and the apparatus relocked into place.

FIG. 5 shows a harness facilitating device designed to be attachable to a medical tube holder apparatus by insertion of latch piece 15 into the opening in an ear 4 of the medical tube holder as shown in FIG. 1. The bridge piece 16 holds the latch piece 15 at one end thereof and contains confined eyelets 17 through which a harness strap 5 may be threaded. Closure pins 19 seated securely in or being a part of base 20 are separated from but attached to bridge piece 16 through a flexible plastic connecting piece 18. In the open position shown in FIG. 5, the harness strap 5 is fully adjustable and moveable.

Figure 6:
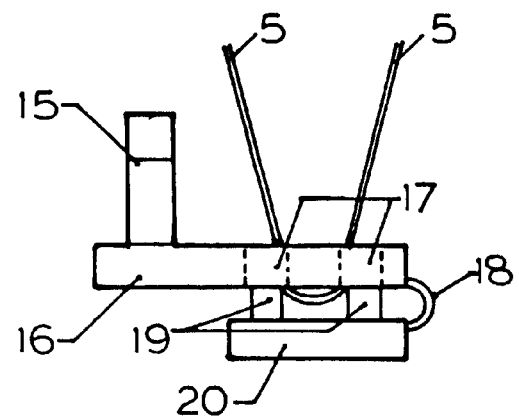
FIG. 6 shows a narrow side view of the device of FIG. 5 in a closed position.

FIG. 6 shows the device of FIG. 5 in a closed position, i.e., the pins 19 have been swung via flexible connecting piece 18 so that they are inserted into eyelets 17 which have previously been threaded with harness strap 5. The pins 19 as wedged into eyelets 17 provide a friction force resulting from sandwiching harness strap 5 between pins 19 and the perimeter of eyelets 17 to prevent further adjustment or movement of strap 5 relative to bridge piece 16. Pins 19 have been designed to fit snugly in eyelets 17 and may even have roughened edges or other friction enhancing characteristics to insure that strap 5 is immobilized relative to bridge piece 16 once the pins 19 have been inserted into eyelets 17.

Figure 7:
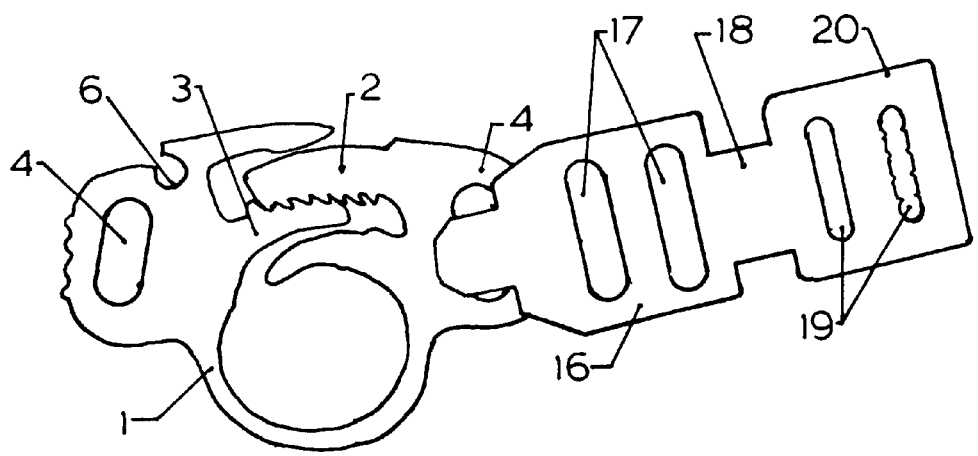
FIG. 7 is a broad side view of the device of FIG. 5 in an open position attached to a medical tube holder apparatus.

FIG. 7 shows the device of FIG. 5, attached to the medical tube holder apparatus of FIG. 1 by insertion of the latch piece 15 (back side only shown) into the opening in ear 4 of the medical tube holder. The eyelets 17 are shown, as are the pins 19 viewed along their lengthwise axis.

Figure 8:
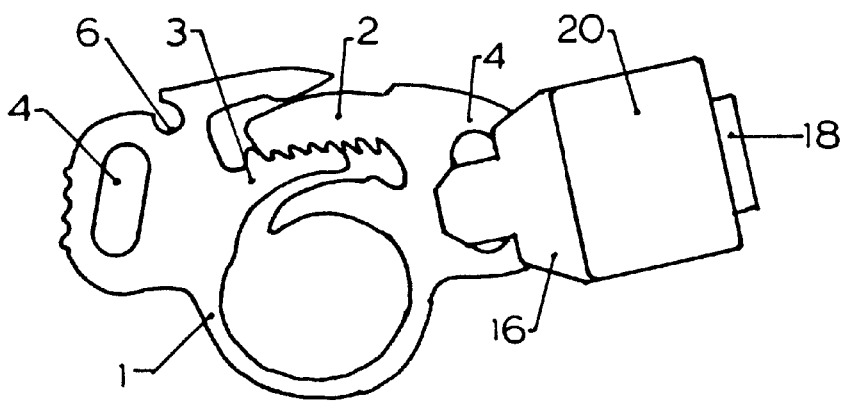
FIG. 8 is a broad side view of the device of FIGS. 5 and 6 in a closed position attached to a medical tube holder apparatus.

FIG. 8 is the same as FIG. 7 except that base 20 and pins 19 have been swung via connecting piece 18 so that the pins are now inserted into the eyelets 17 (covered in this view by the back side of base 20).

Figure 9:
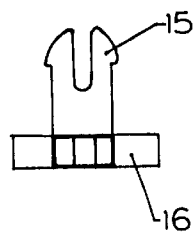
FIG. 9 shows one possible configuration of a latch piece which may be used in securing the device of FIGS. 5 and 6 to a medical tube holder apparatus.

FIG. 9 shows one possible example of a latch piece for use in the harness facilitating device as shown in FIG. 5. As shown, the latch piece 15 has a pair of sturdy but flexible prongs with pointed heads overhanging the stems of said prongs, permitting ease of insertion but the overhang preventing accidental removal, thus effecting the desired latching.

Figure 10:
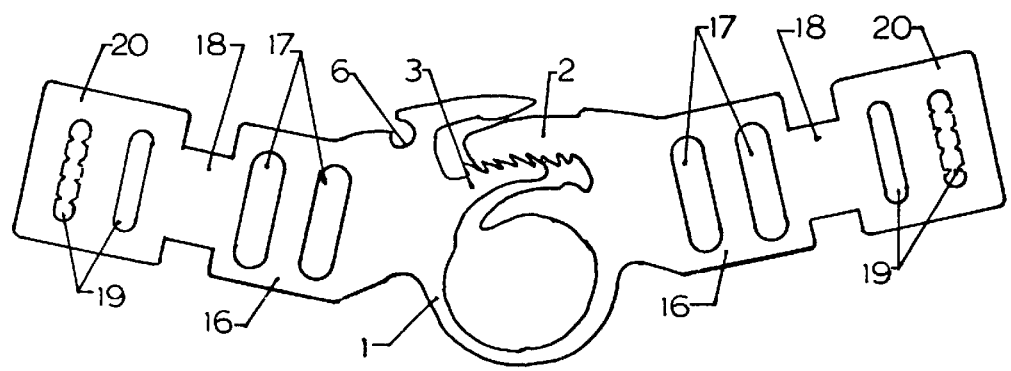
FIG. 10 shows the device of FIGS. 5 and 6 as a nondetachable integral part of a medical tube holder apparatus.

FIG. 10 shows the device of FIG. 5 as an integral, as opposed to an attachable, part of the medical tube holder apparatus of FIG. 1, except that the hole in ear 4 of FIG. 1 is unnecessary and absent from FIG. 10, as is latch piece 15 (shown in FIGS. 5, 6 and 9).

The medical tube holder apparatus as shown in FIG. 1 is designed so that the harness assembly can be attached directly thereto without intervention of a facilitating device such as is shown in FIG. 5. To do so, one would thread a harness strap 5 directly through the holes in ears 4 (FIG. 1). However, the harness strap would not be immobilized relative to the medical tube holder unless clips, stops, knots or similar means were additionally applied to the harness strap. While such means can often be effective and satisfactory, adjustments to the harness assembly or to the position of the medical tube can be made simpler if a means is provided for easy and quick adjustment of the harness strap and equally easy and quick securing of the harness strap in its newly adjusted position.

The facilitating device of FIG. 5 provides a simple means of making necessary adjustments in a harness strap and immobilizing it securely in its newly adjusted position. Whether the facilitating device is a separate, attachable item or is an integral part of the medical tube holder is largely a matter of preference on the part of healthcare professionals working with the patient. Many will probably prefer to attach the medical tube holder apparatus into place around a medical tube serving a patient, then thread the harness strap through two separate identical facilitating devices as the harness assembly is being placed about the head of the patient, and then finally snapping the facilitating device into the medical tube holder to secure the system and anchor the medical tube thereby.

The harness facilitating device and its component parts can be of any material or combination of materials with sufficient resiliency to function as described herein, but probably the most effective and economical option would be high grade, strong but resilient, plastic. The connecting piece 18 as shown in FIGS. 5–8 and 10 can be a flexible plastic strip serving as a living hinge, or it could be any other type hinge, including a traditional metal hinge (although the latter type might not be practical).

A harness assembly would usually be made by looping the harness strap behind the patient's neck, threading the distal ends of the harness strap through respective twin harness facilitating devices and then bringing the harness strap over the patient's ears to the back of the patient's head; a strip of cloth running from the back of the patient's neck to the back of the patient's head near the crown then engage the strap in the neck region and in the back of the patient's head, preferably with velcro-type fasteners at each location. The cloth strip prevents migration of the harness strap from the back of the patient's head forward over the face, while the patient's ears prevent it from migrating downward in the back of the patient's head toward the neck. When the harness facilitating device is snapped into the medical tube holder apparatus, with the harness assembly thus arranged about the patient's neck and head, the medical tube will be held in place and any significant accidental movement or migration thereof will be prevented. The same result would be achieved if the harness facilitating device were an integral part of the medical tube holder.

Obviously, there are numerous ways in which a harness assembly utilizing the medical tube holder apparatus and harness facilitating device as disclosed could be arranged with respect to a patient's head or body which would be effective, in addition to the arrangement mentioned above, and nothing herein is intended to limit the use or utility of the invention herein to any particular harness assembly arrangement.

What is claimed is:

1. A medical tube holder apparatus comprising a one-piece flexible elongated strip clamp means configured transversely to engage frictionally about substantially the entire circumferential cross-section of medical tubes for oral and nasal insertion having radii within a predetermined range, with opposing interlocking extremities accommodating said differing tube radii, and with opposing attaching means integral with said clamp means for affixing a harness means, wherein an upper perimeter portion thereof between the said opposing attaching means contains resilient material with a separation which widens immediately beneath said perimeter to form a c-shaped pocket of resilient but fixed configuration, to receive and maintain in place an auxiliary medical tube.

2. A medical tube holder apparatus according to claim 1 wherein the clamp is a pinch clamp.

3. A medical tube holder apparatus according to claim 2 wherein said opposing attaching means are slotted members.

4. A medical tube holder apparatus according to claim 2 wherein said interlocking extremities respectively consist of a male member with ratchet-like grooves and a female member with opposing ratchet like grooves which permit one-way transverse engagement only and preventing transverse disengagement.

5. A medical tube holder apparatus according to claim 4 wherein said opposing attaching means are slotted members.

6. A medical tube holder apparatus according to claim 5 wherein markings have been affixed respectively to said male member and said female member corresponding by depth of member interlock to at least one radius within a predetermined range of radii for medical tubes of differing radii.

7. A medical tube holder apparatus according to claim 4 wherein markings have been affixed respectively to said male member and said female member corresponding by depth of member interlock to at least one radius within a predetermined range of radii for medical tubes of differing radii.

8. A medical tube holder apparatus according to claim 2 wherein said pinch clamp is a ring clamp.

9. A medical tube holder apparatus according to claim 8 wherein said opposing attaching means are slotted members.

10. A medical tube holder apparatus according to claim 8 wherein said interlocking extremities respectively consist of a male member with ratchet-like grooves and a female member with opposing ratchet like grooves which permit one-way transverse engagement only and preventing transverse disengagement.

11. A medical tube holder apparatus according to claim 10 wherein said opposing attaching means are slotted members.

12. A medical tube holder apparatus according to claim 11 wherein markings have been affixed respectively to said male member and said female member corresponding by depth of member interlock to at least one radius within a predetermined range of radii for medical tubes of differing radii.

13. A medical tube holder apparatus according to claim 10 wherein markings have been affixed respectively to said male member and said female member corresponding by depth of member interlock to at least one radius within a predetermined range of radii for medical tubes of differing radii.

14. A medical tube holder apparatus according to claim 1 wherein said interlocking extremities respectively consist of a male member with ratchet-like grooves and a female member with opposing ratchet like grooves which permit one-way transverse engagement only and preventing transverse disengagoment and said markings have been affixed respectively to said male member and said female member corresponding by depth of member interlock to at least one radius within a predetermined range of radii for medical tubes of differing radii.

15. A medical tube holder apparatus comprising a one-piece flexible elongated strip clamp means configured transversely to engage frictionally about substantially the entire circumferential cross-section of medical tubes for oral and nasal insertion having radii within a predetermined range with opposing interlocking extremities accommodating said differing tube radii, and with opposing attaching means integral with said clamp means for affixing a harness means, wherein said clamp is a pinch clamp, said interlocking extremities respectively consist of a male member with ratchet-like grooves and a female member with opposing ratchet like grooves which permit one-way transverse engagement only and preventing transverse disengagement and markings have been affixed respectively to said male member and said female member corresponding by depth of member interlock to at least one radius within a predetermined range of radii for medical tubes of differing radii.

16. A medical tube holder apparatus according to claim 15 wherein said pinch clamp is a ring clamp.

17. A medical tube holder apparatus according to claim 16 wherein said opposing attaching means are slotted members.

18. A medical tube holder apparatus according to claim 15 wherein said opposing attaching means are slotted members.

19. A harness facilitating device for facilitating the attachment of a harness strap to a medical tube holder apparatus, comprising:
- (i) a means for securely attaching said harness facilitating device to said medical tube holder apparatus;
- (ii) at least two eyelets through which a harness strap can be threaded; and
- (iii) hinged, removable pins sized to fit in frictional engagement within said strap-threaded eyelets.

20. A harness facilitating device according to claim 19, wherein said medical tube holder has a hole therein and wherein the means for attaching said harness facilitating device is a latch piece integral with said harness facilitating device, with prongs having outer peripheral extensions near the end of said prongs sized for latching engagement within said hole.

21. A medical tube holder apparatus comprising a one-piece flexible strip clamp means configured transversely to engage frictionally about substantially the entire circumferential cross-section of medical tubes having radii within a predetermined range, with opposing interlocking extremities accommodating said differing tube radii, and with opposing attaching means integral with said clamp means for affixing a harness means, wherein said attaching means comprises at least two eyelets through which a harness strap can be threaded and hinged, removable pins sized to fit by frictional engagement within said strap-threaded eyelets.

\* \* \* \* \*